United States Patent [19]

Gilligan et al.

[11] Patent Number: 4,797,490

[45] Date of Patent: Jan. 10, 1989

[54] PROCESS FOR THE PREPARATION OF 3-(2'-FLUOROPHENYL)PYRIDINE

[75] Inventors: Paul J. Gilligan, New Haven; Paul R. McGuirk, Gales Ferry, both of Conn.; Michael J. Witty, Dover, Great Britain

[73] Assignee: Pfizer Inc., New York, N.Y.

[21] Appl. No.: 907,176

[22] Filed: Sep. 15, 1986

Related U.S. Application Data

[63] Continuation-in-part of Ser. No. 679,148, Dec. 6, 1984, abandoned.

[51] Int. Cl.$^4$ .............................................. C07D 213/26
[52] U.S. Cl. ..................................... 546/290; 546/296; 546/297; 546/303; 546/304; 546/307; 546/311; 546/339; 546/344; 546/345; 546/346
[58] Field of Search ............... 544/298, 305, 301, 322, 544/325, 242; 546/153, 155, 157, 159, 290, 296, 297, 304, 307, 346, 303, 311, 339, 344, 345

[56] References Cited

U.S. PATENT DOCUMENTS

| | | | |
|---|---|---|---|
| 3,753,993 | 8/1973 | Lesher et al. | 260/286 R |
| 3,907,808 | 9/1975 | Lesher | 424/258 |
| 4,146,625 | 3/1979 | Lee | 424/258 |
| 4,398,029 | 8/1983 | Irikura | 546/156 |
| 4,530,930 | 7/1985 | Uno | 546/156 |
| 4,636,506 | 1/1987 | Gilligan | 514/256 |
| 4,699,984 | 10/1987 | Singh | 546/346 |
| 4,728,654 | 3/1988 | Campbell et al. | 546/157 |

OTHER PUBLICATIONS

Beadle et al. J. Organic Chemistry 1984 49(9), pp. 1594–1603.
March—"Advanced Organic Chemistry" 2nd Edition, pp. 378, 474, 1125.
Greene, "Protective Groups in Organic Synthesis" p. 249.
Negishi, Heterocycles 18, 117–122 (1982).
Roberts, "Basic Principles in Organic Chemistry" 2nd Edition, (1977), p. 575.
Evans, J. of Chem. Soc., Dalton Transactions 1973,(9), pp. 978–981.
Banks, Chemical Abstracts 89:109357k (1978).
Hoffman, "Dehydrobenzene and Cycloalkynes" pp. 46–49, Academic Press, NY (1967).
Pridgen, J. Heterocyclic Chemistry, 1975, 12, p. 443.

*Primary Examiner*—Robert J. Warden
*Assistant Examiner*—Robert Benson
*Attorney, Agent, or Firm*—Peter C. Richardson; Lawrence C. Akers; Gezina Holtrust

[57] ABSTRACT

6-Fluoro-7-pyridylquinolone carboxylic esters and acids having antibacterial activity are prepared by coupling of a 2-fluorophenyl-metallic compound with a pyridyl bromide or iodide in the presence of a transition metal catalyst, nitrating and hydrogenating the pyridyl-2-fluorophenyl compound formed, introducing a substituent on the nitrogen of the amine formed, and cyclizing after reacting with a dialkyl or dibenzyl ethoxymethylene malonate to form a 6-fluoro-7-pyridyl-1,4-dihydroquinol-4-one 3-carboxylate, and hydrolyzing to the corresponding acid.

8 Claims, No Drawings

PROCESS FOR THE PREPARATION OF 3-(2'-FLUOROPHENYL)PYRIDINE

This application is a continuation-in-part of Ser. No. 679,148, filed Dec. 6, 1984, abandoned.

BACKGROUND OF THE INVENTION

This invention relates to a process for the preparation of 6-fluoro-7-pyridyl-1,4-dihydroquinol-4-one 3-carboxylic esters and acids having antibacterial activity and to novel intermediates for use in said process.

U.S. Pat. Nos. 3,753,993 and 3,907,808 describe the preparation of 1,4-dihydro-1-(lower alkyl)-4-oxo-7-(3- or 4-pyridyl)-3-quinolinecarboxylic acids and esters from 3- or 4-(3-aminophenyl)pyridines through ring cyclization after reaction with an appropriate methylene malonate. Although the patents in general disclose compounds having a halogen in the phenyl part of the quinoline, it is noted that there are no examples of their preparation. The only examples are to 7-(substituted-pyridine)derivatives. The known methods for preparing pyridyl-aryl compounds usually convert a suitably substituted benzene derivative by b,uilding up the pyridine ring, as illustrated in the above two patents. These methods often require a considerable number of steps and they are not readily adaptable to the preparation of substituted analogs.

SUMMARY OF THE INVENTION

According to the invention, pyridylaryl compounds are prepared by transition metal catalysed coupling of orthofluorophenylmetal halides with 2-, 3- or 4-halopyridines. Although transition metal catalysed coupling of an arylmetal compound with a heteroaryl bromide or iodide is described by Negishi et al, Heterocycles, 18, 117–122 (1982), it is surprising that this method is successful with ortho-fluoro substituted phenyl metal compounds in view of their known instability. As disclosed by Roberts J. D. et al, Basic Principles of Organic Chemistry, Second Edition (1977), page 575, said orthofluoro compounds decompose rapidly to the corresponding benzyne at room temperature. Nevertheless, the process according to the invention can be successfully worked at temperatures of up to 45° C. required for the coupling reaction to proceed.

Specifically, the invention relates to a process for the preparation of a compound of the formula

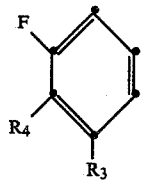

II wherein $R_3$ is hydrogen or halogen; and $R_4$ is 5-pyrimidyl; 6-quinolyl; or 2-pyridyl, 3-pyridyl or 4-pyridyl each of which may be substituted by one or two substituents selected from the group consisting of fluoro, chloro, hydroxy, alkoxy of 1 to 4 carbon atoms, amino, alkylamino of 1 to 4 carbon atoms, dialkylamino of 2 to 8 carbon atoms, carboxy, hydroxyalkyl of 1 to 6 carbon atoms, aminoalkyl of 1 to 6 carbon atoms and said hydroxy, amino, carboxy, hydroxyalkyl and aminoalkyl in suitably protected form, by reacting a phenylmetallic compound of the formula

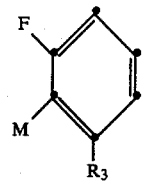

wherein $R_3$ is as defined above and M is a metal or a metal containing group, with a compound of the formula $R_4$ Hal wherein $R_4$ is as defined above and Hal is bromo or iodo, preferably bromo, in the presence of a transition metal catalyst.

The invention is also in the process for the preparation of antibacterial agents of the formula

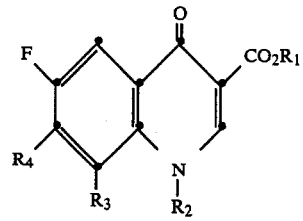

I wherein
$R_1$ is hydrogen, alkyl of 1 to 3 carbon atoms or benzyl;
$R_2$ is alkyl or haloalkyl of 1 to 3 carbon atoms, allyl, alkyl, cyclopropyl, hydroxyethyl, phenyl or 4-fluorophenyl; and
$R_3$ and $R_4$ are as defined above by cyclizing a compound of the formula

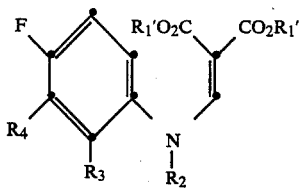

IX wherein $R_1'$ is alkyl of 1 to 3 carbon atoms or benzyl and $R_2$, $R_3$ and $R_4$ are as defined above, and hydrolyzing when $R_1'$ is alkyl or benzyl, or hydrogenolyzing, when $R_1'$ is benzyl, to obtain the corresponding compound wherein $R_1$ is hydrogen.

The invention further comprises the novel intermediates of formula IX above and of formula X as follows:

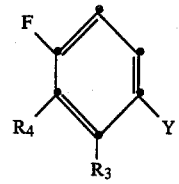

X wherein $R_3$ and $R_4$ are as defined above and Y is hydrogen, nitro, amino, —$NHR_2$ wherein $R_2$ is as defined above, —NHC(O)R wherein R is alkyl of 1 to 3 carbon atoms, or —NR$_2$C(O)R wherein R$_2$ and R are as defined above.

The invention includes processes for preparing the intermediates of formula IX and X, substantially as shown in reaction Scheme A hereafter. The preparation of compounds of formula X in which Y is hydrogen (formula II) is described above.

The compounds of formula X in which Y is nitro (formula III) ar,e prepared by reacting a compound of formula II with a nitrating agent, such as a mixture of concentrated nitric acid and concentrated sulfuric acid.

The compounds of formula X in which Y is amino (formula IV) are prepared by reducing a compound of formula III.

The compounds of formula X in which Y is —NHC(O)R (formula V) are prepared by reacting a compound of formula IV with an alkanoyl halide or anhydride of 2 to 4 carbon atoms. The compounds of formula V formed react with a R$_2$-containing halide, tosylate or mesylate to form the compounds of formula X in which Y is —NR$_2$C(O)R (formula VI). The formed compounds of formula VI provide compounds of formula X in which Y is —NHR$_2$ (formula VII) on hydrolysis.

The compounds of formula IX are prepared by reacting compounds of formula VII with dialkyl or dibenzyl alkoxy methylene malonate wherein the alkoxy and each alkyl in said dialkyl has from 1 to 3 carbon atoms

DETAILED DESCRIPTION OF THE INVENTION

The coupling process of the invention is generally carried out in a reaction-inert solvent, i.e. a solvent which does not interfere with the coupling reaction of the arylmetallic compound with the 2-, 3- or 4-halopyridine. Suitable reaction inert solvents are ethers, e.g. dialkylethers such as diethylether and dipropylether, and cyclic ethers such as tetrahydrofuran (THF) and dioxane Co-solvents may be used with the ethers if desired, e.g. to enhance the solubility therein of the reaction materials. Examples of suitable cosolvents are aliphatic and aromatic hydrocarbons containing from 6 to 10 carbon atoms, e.g. benzene or toluene. Other suitable cosolvents besides the hydrocarbons are cosolvent complexing agents such as tetramethylethylenediamine (TMEDA) and hexamethylphosphorictriamide (HMPA) as known to those skilled in the art.

The transition metal catalyst is generally used in an amount of 0.5 to 10 mole %.

The transition metal catalyst may be of the 0 or II oxidation state and contains a transition metal, that is a metal selected from Groups Ib through VIIb and VIII of the Periodic Table as set out in Lange's Handbook of Chemistry, Eleventh Edition. Suitable metals are for instance platinum, cobalt, iron, zirconium, molybdenum, ruthenium, manganese and rhodium, and preferably, palladium, platinum and nickel.

The transition metal is combined with a ligand to form the catalyst. Suitable known ligands are (PPh$_3$)$_2$, (PPh$_3$)$_4$, P(CH$_3$)$_3$, P(C$_2$H$_5$)$_3$, Ph$_2$P(CH$_2$)$_n$PPh$_2$ wherein n is an integer from 1 to 4, (CH$_3$)$_2$ P(CH$_2$)$_2$ P(CH$_3$)$_2$, cis Ph$_2$CH=CHPh$_2$, P(o-tolyl)$_3$, P(o-xylyl)$_3$, acetonylacetonate, 2,2'-bipyridyl pyridine, wherein Ph is phenyl, and others as described by Tamao et al, Bull. Chem. Soc. Japan, 49 (7), 1959 (1976). Other transition metal catalysts are disclosed by A. Sekiya et al, J. Organometal Chem 118, 349–354 (1976) and E. Negishi, Acc. Chem Res., 15, 340–348 (1982) and references cited therein The preferred transition metal catalysts are (PPh$_3$)$_2$ Ni X$_2$, (PPh$_3$)$_4$Ni, (PPh$_3$)$_2$PdX$_2$ and (PPh$_3$)$_4$Pd wherein X is chloro, bromo or iodo and Ph is phenyl. The most preferred catalyst is tetrakis(triphenylphosphine)palladium.

The reaction temperature of the coupling process ranges from room temperature to 50° C.

The phenylmetal compounds containing group M may be prepared by known methods. For instance, they may be prepared from a 2-F,6-R$_3$-phenylhalide in which the halide is chloro, bromo or iodo and R$_3$ is as defined above by direct lithium-halogen exchange using n-butyl, sec-butyl or t-butyl lithium followed by transmetallation by a wide variety of salts by known methods such as described by E. Negishi, Organometallics,in Organic Synthesis, Vol. 1, page 104. The salts used in the transmetallation may be selected from the salts of zinc, cadmium, magnesium, mercury, tin, silver, copper and aluminum, preferably zinc. The most commonly used salts are the halides, particularly chlorides, bromides, and iodides, and cyanides such as copper cyanide. The most advantageous salt is zinc chloride. The transmetallation is at —78° to +70° C., preferably —78° to —50°.

The above treatment with a butyl lithium compound is generally carried out at —100° to —50° C., usually at —78° to —70° C., in a suitable solvent such as ethers alone or in admixture with an aliphatic or aromatic hydrocarbon solvent having from 6 to 10 carbon atoms. Suitable ethers are for instance dialkylethers such as diethylether, cyclic ethers such as THF, and dimethoxyethane. Suitable hydrocarbon solvents are for instance toluene and benzene. The treatment with the butyl lithium is best carried out in THF at —78° to —70° C.

The phenylmetal compounds may also be prepared by direct reaction of the corresponding 2-F,6-R$_3$-phenyl halide with a metal in the zerovalent state. Useful metals in the zerovalent state are alkali metals such as lithium, sodium and potassium, alkaline earth metals such as magnesium, and transition metals such as zinc. The reaction temperatures may range from —100° C. for very active metals to 25° C. Again, solvents of use in this process are ethers alone or in admixture with hydrocarbons having 6 to 10 carbon atoms such that at least one equivalent of the ether is present.

Alternatively, the phenylmetal compounds may be formed by hydrogen-metal exchange between a corresponding 2-F,6-R$_3$-phenyl compound and a strong base such as n-butyllithium, t-butoxide-butyllithium, TMEDA-butyllithium, or lithium or potassium hexamethyldisilizane.

The phenylmetal compound containing group M is generally not isolated bef,ore reaction by coupling with a 2-, 3 or 4-halopyridine.

The coupling compound of formula II is then converted into compounds of formula I' as depicted in reaction Scheme A hereinafter.

The nitration to compounds of formula III and the reduction to anilines of formula IV are conducted by standard methods, for instance as described by March J., Adv. Org. Chem., Second edition, McGraw Hill, (1977) at page 474 and 1125, respectively.

The N-R$_2$-substituted compounds of formula VII may be formed by several methods known in the art.

Scheme A

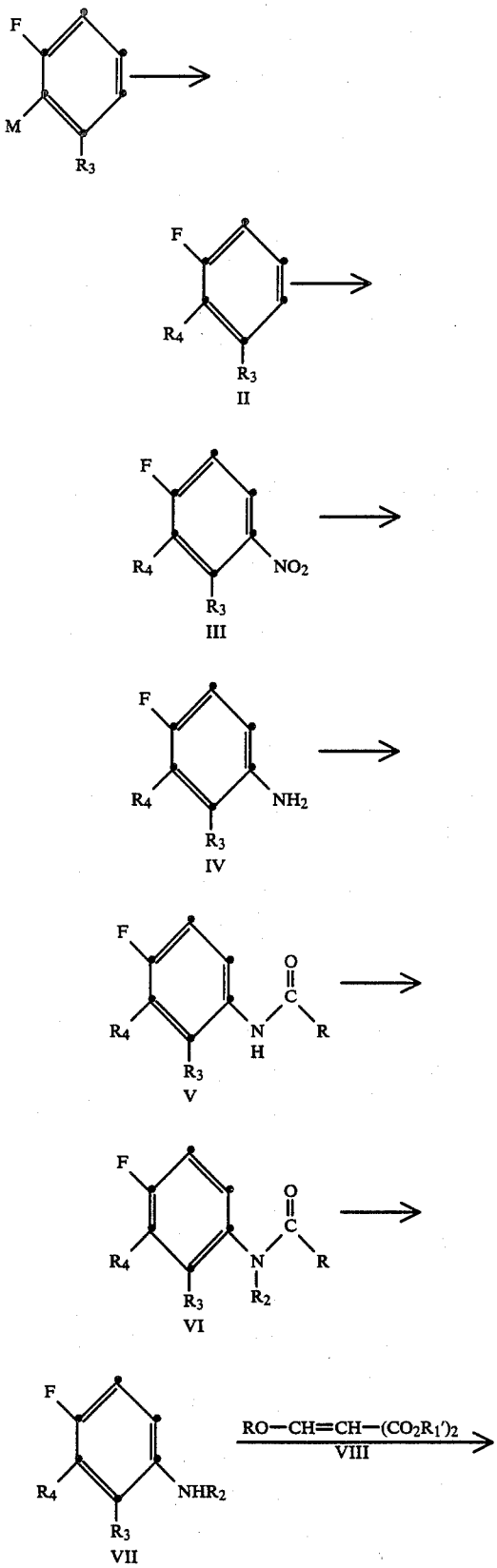

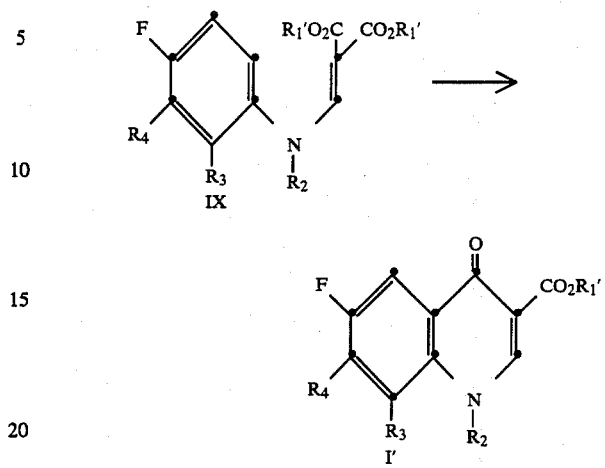

The compounds of formula VII may be formed for instance as shown in Scheme A by reacting first with an alkanoyl anhydride or halide having 1 to 3 carbon atoms in the alkyl group to form compounds of formula V in which R is alkyl of 1 to 3 carbon atoms. The reaction may for instance be with acetic anhydride in ethanol at 25 to 100° C. The compound of formula V is reacted with a suitable base such as sodium hydride and then N-substituted with an appropriate halide, tosylate or mesylate containing group $R_2$. The N-substitution is generally carried out in a polar solvent such as diglyme, THF, dimethylformamide (DMF), dimethylacetamide (DMA) or dimethylsulfoxide (DMSO), preferably DMF. The alkanoyl group —C(O)R in the compound of formula VI is removed by refluxing in aqueous medium such as 6N hydrochloric acid to form the compoundoof formula VII.

Alternatively, the N-substituted anilines of formula VII wherein $R_2$ is alkyl may be prepared by reductive amination with an appropriate aldehyde and a suitable reducing agent such as diborane, palladium or carbon with hydrogen, sodium borohydride or sodium cyanoborohydride as for instance described in the above March reference at pages 819 and 820. N-ethyl substituted anilines of formula VII wherein $R_2$ is ethyl may also be formed by treatment of anilines of formula IV with $NaBH_4$ in acetic anhydride in accordance with March at page 820. Another method is described in March, at page 1122 involving reduction with appropriate reducing agents such as lithium aluminum hydride of amides of formula VI and yet another method is the Eschweiler-Clarke procedure using formic acid and a corresponding aldehyde of formula RCHO in which R is hydrogen or alkyl or haloalkyl of 1 to 5 carbon atoms, as described at page 820 of March.

The substituted aniline of formula VII in which $R_2$, $R_3$ and $R_4$ are as defined above is reacted with a dialkylor dibenzyl alkoxymethylene malonate of formula VIII wherein the alkoxy group OR has from 1 to 6 carbon atoms and $R_1'$ is alkyl of 1 to 6 carbon atoms or benzyl The reaction is generally carried out without solvent at about 100° to 200° C., preferably 150° to 175° C., for about 0.5 to 24 hours, usually for 0.5 to 2 hours The resulting intermediates of formula IX are crystallized from a hydrocarbon or ethereal solvent such as light petroleum or diethyl ether, respectively, and cyclized.

The cyclization is by heating in an acidic medium such as polyphosphate ester at about 100° to 250° C. for about 0.5 to 24 hours, preferably at 100° to 150° C. for 0.5 to 2 hours. This procedure is described by Albrecht, R., Prog. Drug Res., Vol. 21, 35–49 (1977). Instead of polyphosphate ester, one may use phosphorus oxychloride, phosphorus pentachloride, thionyl chloride, $P_2O_5/MeSO_3H$, concentrated sulfuric acid or polyphosphoric acid.

Alternately, when $R^2=H$, the cyclization is by heating at about 100° to 250° C. in high boiling solvents such as dichlorobenzene, tetralin, diphenylether or diethyleneglycol dimethylether, preferably Dowtherm A which is a commercially available high boiling solvent mixture of diphenylether and diphenyl. The reaction time ranges from about 0.5 to 2 hours, preferably 0.5 to 1 hour. The compounds wherein $R^2$ is alkyl are prepared by standard alkylation such as alkyl iodide reaction in the presence of $K_2CO_3$ in DMF.

The resulting ester of formula I' is usually purified by recrystallization or chromatography.

The corresponding acid of formula I in which $R_1$ is hydrogen may be obtained from the ester of formula I' by conventional hydrolysis such as heating in base or acid, for instance hydrochloric acid or hydrogenolysis when $R_1'$ is benzyl by conventional methods such as reaction with Pd/C in a hydrogen atmosphere in a solvent such as ethanol or ethyl acetate.

The suitably protected forms mentioned above with respect to certain substituents in group $R_4$ are those conventionally used by those skilled in the art. Well-known protected forms are ethers having 1 to 6 carbon atoms in the ether to protect hydroxy and hydroxyalkyl, esters having 1 to 6 carbon atoms in the ester group to protect carboxy and amides having 1 to 6 carbon atoms to protect amino and aminoalkyl The protecting groups may be removed by conventional methods such as hydrolysis with acid or base, specifically Lewis acid in the case of the ether protecting groups.

The following examples illustrate the invention.

EXAMPLE 1

4-(2,6-Difluorophenyl)-pyridine (A) A 1.6M solution of n-butyl lithium (14 ml) was added dropwise to a stirred solution of 1,3-difluorobenzene (2.17 g) in 34 ml dry tetrahydrofuran at −78° C. After 1 hour at −78° C., the solution was warmed to −50° C. and a solution of anhydrous zinc chloride (3.0 g) in 34 ml tetrahydrofuran was added. After a further 20 minutes at −50° C., a solution of 4-bromopyridine (1.62 g) in 10 ml ether was added, followed by 1.0 g of tetrakis(triphenylphosphine) palladium. The solution was then allowed to warm slowly to room temperature and it was then heated at 40° C. for 12 hours. The mixture was cooled to room temperature and it was first quenched with saturated aqueous ammonium chloride and then extracted with ethyl acetate. The organic extracts were dried and evaporated yielding a yellow crystalline solid. This material was purified by elution on silica gel with ethyl acetate/hexanes to give 1.4 g (73% yield) of the required product as a pale yellow solid of m.p. 113°–114° C. NMR (CDC13, 60 MHz): 8.65 (m, 2H), 6.8–7.6 (m, 5H).

4-(2,6-Difluoro-3-nitrophenyl)-pyridine (B) A mixture of cold (0° C.) concentrated nitric acid (20.4 ml) and concentrated sulfuric acid (20.4 ml) was added in portions to a stirred solution of 10 g 4-(2,6-difluorophenyl)-pyridine in 56 ml concentrated sulfuric acid at 0° C. After 45 minutes at 0° C., the mixture was poured onto ice and the resulting solution was neutralized with solid sodium bicarbonate. The neutralized solution was then extracted twice with ethyl acetate and the organic extracts were dried and evaporated to give the product as a white solid of m p. 110°–112° C. (10.9 g, 88% yield). NMR (CDC13, 60 MHz): 8.8 (m, 2H), 8.2 (m, 1H), 7.0–7.6 (m, 3H).

4-(3-Amino-2,6-difluorophenyl)-pyridine (C) A solution of 4-(2,6-difluoro-3-nitrophenyl)pyridine (10.9 g) in ethanol (500 ml) was hydrogenated (at 50 p.s.i.) for 1 hour over 15 g of Raney Nickel The reaction mixture was then filtered through Supercel and the filtrate was evaporated in vacuo to give the product as a white solid of m.p. 190°–192° C. (6.6 g, 68% yield). MS calcd. for C11H8F2N2: 206.0654. Found: 206.0661. NMR, (CDC13, 60 MHz): 8.7 (m, 2H), 7.5 (m, 2H), 6.9 (m, 2H).

4-(3-Acetylamino-2,6-difluorophenyl)-pyridine (D) A mixture of 4-(3-amino-2,6-difluorophenyl)pyridine (6.5 g), acetic anhydride (4.9 g) and ethanol (200 ml) was heated at reflux. After 1 hour, a further 3.3 ml acetic anhydride was added and a third portion (1.5 ml) after another 3.5 hours. Reflux was continued for a total of 6 hours after which time the solution was cooled and evaporated and the residue was partitioned between aqueous sodium bicarbonate and chloroform. The organic layer was washed with water, dried and evaporated to give the solid product of m.p. 148°–150° C. (6.8 g, 86% yield). NMR (CDC13, 60 MHz): 8.8 (m, 2H), 8.05 (m, 2H), 7.4 (m, 2H), 6.9 (m, 1H), 2.2 (s, 3H).

N-Ethyl 2,4-difluoro-3-(4-pyridyl)-acetanilide (E) 4-(3-Acetylamino-2,6-difluorophenyl)-pyridine (6.8 g) was added portionwise to a stirred mixture of iodoethane (4.68 g) and 50% sodium hydride dispersion (1.44 g) in 65 ml N,N-dimethylformamide at 0° C. Once evolution of hydrogen was finished the mixture was stirred for 1 hour at room temperature. It was then poured onto iced water and the mixture was extracted twice with ethyl acetate. The combined organic extracts were washed with water, dried and evaporated, yielding the product as a solid of m.p. 119°–121° C. (6.6 g, 87% yield). NMR (CDC13, 60 MHz): 8.65 (m, 2H), 7.5–7.0 (m, 4H), 3.6 (qt, 2H, J=6.5 Hz), 1.95 (s, 3H), 1.1 (t, 3H, J =6.5 Hz)

N-Ethyl 2,4-difluoro-3-(4-pyridyl)-aniline (F) A mixture of N-ethyl 2,4-difluoro-3-(4-pyridyl)acetanilide (6.6 g) and 60 ml 6M hydrochloric acid was heated at reflux for 2 hours. The mixture was cooled, extracted once with chloroform and the aqueous phase was neutralized,with 30% aqueous sodium hydroxide It was then extracted twice with chloroform and the combined organic extracts were dried and evaporated yielding the product as a pale brown oil (5.6 g) which was used immediately without further purification or characterization.

Diethyl 2,4-difluoro-(N-ethyl)-3-(4-pyridyl)anilinomethylene malonate (G) A mixture of 5.6 g of N-ethyl 2,4-difluoro-3-(4-pyridyl)-aniline and 5.19 g diethyl ethoxymethylene malonate was heated at 150° C. for 1 hour. The reaction mixture was then cooled and the resulting solid was washed well with petroleum ether to give the product as a pale brown solid of m.p. 104°–106° C. (7.31g, 75% yield) NMR (CDC13, 250 MHz): 8.75 (d, 2H, J=5 Hz), 7.65 (s, 1H), 7.45 (m, 2H), 7.25 (m, 1H), 7.05 (m, 1H), 4.2 (qt, 2H, J=6 Hz), 3.75 (2qt, 4H, J=6 Hz), 1.25 (t, 6H, J=6 Hz), 1.1 (t, 3H, J=6 Hz).

MS calcd. for C21H22F2N2O4: 404.1548. Found 404.1526.

Ethyl 1-ethyl-6,8-difluoro-7-(4-pyridyl)-1,4-dihydroquinol-4-one 3-carboxylate (H) A mixture of 35 ml polyphosphate ester and 3.5 g diethyl 2,4-difluoro-N-(ethyl)-3-(4-pyridyl)-anilinomethylene malonate was heated at 150° C. for 20 minutes The reaction mixture was cooled, 100 ml water was added and the mixture was neutralized with solid sodium bicarbonate. This mixture was then stirred in the presence of excess sodium bicarbonate for 2 hours. The resulting precipitate was collected by filtration, washed well with water and then dissolved in chloroform. The formed solution was dried and evaporated, yielding 2.0 g of the product as a yellow solid (65% yield). NMR (CDC13, 250 MHz): 8.8 (m, 2H), 8.5 (s, 1H), 8.2 (dd, 1H, J=9 Hz and 2 Hz), 7.45 (m, 2H), 4.45 (2qt, 4H), 1.45 (t, 3H, J=6 Hz), 1.35 (t, 3H, J=6 Hz).

MS calcd. for C19H16F2N2O3: 358.1129. Found 358.1109.

1-Ethyl-6,8-difluoro-7-(4-pyridyl)-1,4-dihydroquinol-4-one 3-carboxylic acid (I) A mixture of 1.28 g ethyl 1-ethyl-6,8-difluoro-7-(4-pyridyl)-1,4-dihydroquinol-4-one 3-carboxylate and 15 ml 2M hydrochloric acid was heated at reflux for 1 hour. The reaction mixture was then cooled in ice and the resulting precipitate was collected by filtration, washed with water, then ether and dried. The solid was dissolved in the minimum quantity of 1M sodium hydroxide and the resulting solution was acidified with acetic acid. The precipitate was collected by filtration, washed with water and dried, yielding the product as a white solid of m.p.>260° C. (1.22 g, 93% yield). NMR (DMSO-d6/Trifluoroacetic acid-d, 250 MHz): 9.2 (d, 2H, J=4.5 Hz), 9.1 (s, 1H), 8.4 (d, 2H, J=4.5 Hz), 8.2 (dd, 1H, J=7 Hz and 2 Hz), 4.7 (m, 2H), 1.5 (t, 3H, J=6 Hz).

Anal: calcd. for C17H12F2N2O3.0.25H2O: C, 60.98; H, 3.74; N, 8.37%. Found: C, 60.60; H, 3.64; N, 8.21%

EXAMPLE 2

3-(2,6-Difluorophenyl)-pyridine (A) The title compound was made by the method of Example 1A. 11.00 g (77% yield) were prepared from 1,3-difluorobenzene (12.8 g), anhydrous zinc chloride (20.48 g), 3bromopyridine (11.85 g) and tetrakis(triphenylphosphine) palladium (5.0 g). The product is a pale yellow solid of m.p. 194°–196° C. NMR (CDC13, 60 MHz): 9.1 (m, 2H), 7.0–8.4 (m, 5H).

3-(2,6-Difluoro-3-nitrophenyl)-pyridine (B) 9.13 g (56% yield) was prepared by the method of Example 1B from 13.2 g of 3-(2,6-difluorophenyl)-pyridine. The product is a white solid of m.p. 68°–70° C. NMR (CDC13, 60 MHz): 8.8 (m, 2H), 8.2 (m, 1H), 7.0–7.6 (m, 3H).

3-(3-Amino-2,6-difluorophenyl)-pyridine (C) 7.1 g (90% yield) was prepared by the method of Example 1C from 3-(2,6-difluoro-3-nitrophenyl)-pyridine (9.0 g). The product was a white solid of m.p. 112°–113° C.

3-(3-Acetylamino-2,6-difluorophenyl)-pyridine (D) 7.03 g (98% yield) was prepared by the method of Example 1D from 3-(3-amino-2,6-difluorophenyl)-pyridine (6.5 g). M.p. 154.5°–155° C. NMR (CDC13, 60 MHz): 8.65 (m, 2H), 6.8–8.5 (m, 4H), 2.3 (s, 3H).

N-Ethyl 2,4-difluoro-3-(3-pyridyl)-acetanilide (E) 7.78 g (100% yield) was prepared by the method of Example 1E from 3-(3-acetylamino-2,6-difluorophenyl)pyridine (7.00 g). The brown oil formed was used directly without further purification. NMR (CDC13, 60 MHz): 9.25 (m, 2H), 7.5–8.0 (m, 4H), 4.1 (qt, 2H, J=6.5 Hz), 2.3 (s, 3H), 1.6 (t, 3H, J=6.5 Hz).

N-Ethyl 2,4-difluoro-3-(3-pyridyl)-aniline (F) 7.08 g (92% yield) was prepared by the method of Example 1F from N-ethyl 2,4-difluoro-3-(3-pyridyl)acetanilide (8.35 g). White solid of m.p. 79°–80° C. NMR (CDC13, 60 MHz): 8.8 (m, 2H), 7.9 (m, 1H), 7.5 (m, 1H), 6.5–7.2 (m, 2H),, 3.3 (qt, 2H, J=6.5 Hz), 1.5 (t, 3H, J=6.5 Hz).

Diethyl 2,4-difluoro-N-(ethyl)-3-(3-pyridyl)anilinomethylene malonate (G) 8.9 g (75% yield) was made by the method of Example 1G from 6.3 g N-ethyl 2,4-difluoro-3-(3-pyridyl)-aniline NMR (CDC13, 60 MHz): 8.8 (m, 2H), 8.1 (m, 1H), 7.8 (s, 1H), 7.7–7.0 (m, 3H), 4.4 (qt, 2H, J=6.5 Hz), 3.9 (2qt, 4H, J=6.5 Hz), 1.5 (t, 6H, J=6.5 Hz), 1.4 (t, 3H, J=6.5 Hz).

Ethyl 1-ethyl-6,8-difluoro-7-(3-pyridyl)-1,4-dihydroquinol-4-one 3-carboxylate (H) 0.88 g (26% yield) was made by the method of Example 1H from 1.00 g 2,4-difluoro-N-ethyl-3-(3-pyridyl)-anilinomethylene malonate as a yellow solid of m.p. 141°–143° C. NMR (CDC13, 250 MHz): 8.75 (m, 2H), 8.45 (s, 1H), 8.2 (d, 1H, J=9 Hz), 7.8 (m, 1H), 7.5 (m, 1H). 4.4 (2q, 4H), 1.5 (t, 3H, J=6.5 Hz), 1.4 (t, 3H, J=6.5 Hz).

1-Ethyl-6,8-difluoro-7-(3-pyridyl)-1,4-dihydroquinol-4-one 3-carboxylic acid hydrochloride salt (I) A mixture of ethyl 1-ethyl-6,8-difluoro-7-(3-pyridyl)-1,4-dihydroquinol-4-one 3-carboxylate (1.1 g) and 20 ml 2M hydrochloric acid was heated at reflux for 0.5 hours The reaction mixture was cooled and the resulting precipitate was collected by filtration, washed with water and dried, yielding the product as a white solid of m.p. >270° C. (930 mg, 85% yield). NMR (DMSO-d6/Trifluoroacetic acid-d, 250 MHz): 9.3 (m, 2H), 9.1 (d, 1H, J=6 Hz), 8.95 (d, 2H, J=7 Hz), 8.4 (m, 1H), 4.95 (m, 2H), 1.7 (t, 3H, J=6 Hz).

Anal: Calcd. for C17H12F2N2O3.HCl: C, 55.73; H, 3.55; N, 7.65%. Found: C, 55.84; H, 3.59; N, 7.66%.

EXAMPLE 3

2-(2,6-D-fluorophenyl)-pyridine (A) The title compound was made by the method of Example 1A. 5.43 g (79% yield) were prepared from 1,3-difluorobenzene (6.15 g), anhydrous zinc chloride (8.55 g), 2bromopyridine (5.69 g) and tetrakis(triphenylphosphine) palladium (2.5 g). The product is a pale yellow oil. NMR (CDC13, 250 MHz): 8.76 (dq, 1H), 7.8 (td, 1H), 7.5 (dt, 1H), 7.36 (m, 2H), 7.01 (m, 2H).

2-(2,6-Difluoro-3-nitrophenyl)-pyridine (B) 6.5 g (96% yield) was prepared by the method of Example 1B from 5.43 g of 2-(2,6-difluorophenyl)-pyridine. The product is a white solid of m.p. 84°–86° C. NMR (CDC13, 250 MHz): 8.8 (m, 2H), 8.2 (m, 1H), 7.9 (m, 1H), 7.5 (m, 1H), 7.4 (m, 1H), 7.2 (m, 1H).
MS: Calcd. for C11H6F2N2O2: 236.0398. Found: 236.0398.

2-(3-Amino-2,6-difluorophenyl)-pyridine (C) 5.0 g (88% yield) was prepared by the method of Example 1C from 2-(2,6-difluoro-3-nitrophenyl)-pyridine (6.5 g). The product was a white solid of m.p. 71°–73° C. NMR (CDC13, 250 MHz): 8.75 (m, 1H), 7.8 (m, 1H), 7.5 (m, 1H), 7.3 (m, 1H), 6.8 (m, 2H).

2-(3-Acetylamino-2,6-difluorophenyl)-pyridine (D) 4.96 g (83% yield) of the title compound was prepared by the method of Example 1D from 2-(3-amino-2, 6-difluorophenyl)-pyridine (5.0 g); the compound is a white solid of m.p. 132°–133° C. NMR (CDC13, 250 MHz): 8.75 (d, 1H, J=6 Hz), 8.2 (m, 1H), 7.8 (m, 2H), 7.45 (d, 1H, J=9 Hz), 7.3 (m, 1H), 6.95 (m, 1H), 2.25 (s, 3H).
MS: Calcd. for C13H10F2N2O: 248.0761. Found: 248.0803.

N-Ethyl 2,4-difluoro-3-(2-pyridyl)-acetanilide (E) 5.52 g (100% yield) was prepared by the method of Example 1E from 2-(3-acetylamino-2,6-difluorophenyl)pyridine (4.96 g). The pale green oil formed was chromatographed on silica gel with ethyl acetate to give a white solid of m.p. 44.5°–75.5° C. NMR (CDC13, 250 Hz): 9.78 (dt, 1H), 7.85 (td, 1H), 7.5 (dt, 1H), 7.35 (qd, 1H), 7.25 (6 line multiplet, 1H), 7.09 (td, 1H), 3.75 (10 line multiplet, 2H), 1.9 (s, 3H), 1.13 (t, 3H, J=7 Hz).

N-Ethyl 2,4-difluoro-3-(2-pyridyl)-aniline (F) 3.6 g (77% yield) was prepared by the method of Example 1F from N-ethyl 2,4-difluoro-3-(2-pyridyl)acetanilide (5.52 g). White solid of m.p. 80°–81° C. NMR (CDC13, 250 MHz): 8.8 (m, 1H), 7.8 (m, 1H), 7.5 (m, 1H), 7.3 (m, 1H), 6.9 (m, 1H), 6.7 (m, 1H), 3.23 (qt, 2H, J=6.5 Hz), 1.3 (t, 3H, J=6.5 Hz).
MS: Calcd. for C13H12F2N2: 234.0969. Found 234 0964.

Diethyl 2,4-difluoro-N-(ethyl)-3-(2-pyridyl)anilinomethylene malonate (G) 5.1 g (82% yield) was made by the method of Example 1G from 3.6 g N-ethyl 2,4-difluoro-3-(2-pyridyl)-aniline The product was purified by elution on silica gel with 60% ethyl acetate/hexane and 1% triethylamine. Colorless oil was formed. NMR (CDCl3, 250 MHz): 8.8 (m, 1H), 7.8 (m, 1H), 7.65 (s, 1H), 7.55 (m, 1H), 7.35 (m, 1H), 7.2 (m, 1H), 7.0 (m, 1H), 4.2 (qt, J=6.5 Hz), 3.7 (2qt, 4H, J=6.5 Hz), 1.2 (t, 6H, J=6.5 Hz), 1.1 (t, 3H, J=6.5 Hz).

1-Ethyl 1-ethyl-6,8-difluoro-7-(2-pyridyl)-1,4-dihydroquinol-4-one 3-carboxylate (H) 1.75 g (71% yield) was made by the method of Example 1H from 2.77 g 2,4-difluoro-N-ethyl-3-(2-pyridyl)-anilinomethylene malonate as a yellow solid of m.p. 159°–160° C. NMR (CDC13, 250 MHz): 8.8 (m, 1H), 8.45 (s, 1H), 8.2 (d, 1H, J=9 Hz), 7.85 (m, 1H), 7.55 (m, 1H), 7.4 (m, 1H), 4.4 (2q, 4H), 1.5 (t, 3H, J=6.5 Hz), 1.4 (t, 3H, J=6.5 Hz)

1-Ethyl-6,8-difluoro-7-(2-pyridyl)-1,4-dihydroquinol-4-one 3-carboxylic acid (I) A mixture of ethyl 1-ethyl-6,8-difluoro-7-(2-pyridyl)-1,4-dihydroquinol-4-one 3-carboxylate (1.08 g) and 20 ml 2M hydrochloric acid was heated at reflux for 0.5 hours. The reaction mixture was cooled and the resulting precipitate was collected by filtration, washed with water and dried, yielding the hydrochloride of the product as a white solid. The solid was dissovled in water by adding the minimum requried amount of 1M sodium hydroxide, the pH was adjusted to 3 by the addition of glacial acetic acid and the resutling precipitate was collected by filtration, washed with water and dried, yielding the product as a white solid of m.p. 242°–243° C. (997 mg, 86% yield). NMR (DMSO-d6/Trifluoroacetic acid-d, 250 MHz); 9.1 (m, 1H), 8.95 (s, 1H), 8.75 (m, 1H), 8.3 (m, 1H), 8.2 (m, 1H), 4.65 (m, 2H), 1.6 (t, 3H, J=6 Hz).
Anal: Calcd for C17H12F2N2O3 1.25H2O: C, 57.87; H, 4.11; N, 7.94%. Found: C, 57.88 H, 3.46; N, 7.97%.
MS: Calcd. for C17H12F2N2O3: 330.0816. Found: 330.0812.

We claim:
1. A process for preparing a compound of the formula

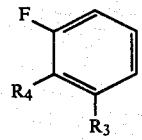

wherein R3 is hydrogen or fluoro; and R4 is 3-pyridyl which may be substituted by one or two substituents selected from the group consisting of fluoro, chloro, hydroxy, alkoxy of 1 to 4 carbon atoms, amino, alkylamino of 1 to 4 carbon atoms, dialkylamino of 2 to 8 carbon atoms, carboxy, hydroxyalkyl of 1 to 6 carbon atoms, aminoalkyl of 1 to 6 carbon atoms and, said hydroxy, amino, carboxy, hydroxyalkyl, aminoalkyl in suitably protected form, which comprises reacting at room temperature to 50° C. a phenylzinc compound of the formula

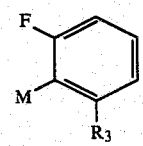

wherein $R_3$ is as defined above and M is zinc or a zinc halide group, with a compound of the formula $R_4$ Hal wherein $R_4$ is as defined above and Hal is bromo or iodo in the presence of a transition metal catalyst complex comprising a transition metal in the (0) or (II) oxidation state and a phosphine containing ligand, and removing any protecting group in any of the above suitably protected forms.

2. A process as claimed in claim 1 wherein $R_3$ is fluoro.

3. A process as claimed in claim 1 wherein said reaction is carried out in an ether solvent.

4. A process as claimed in claim 3 wherein said ether solvent is selected from the group consisting of iethylether and tetrahydrofuran.

5. A process as claimed in claim 1 wherein said zinc halide group is $ZnCl$.

6. A process as claimed in claim 1 wherein said transition metal in said catalyst is selected from the group consisting of cobalt, iron, zirconium, molybdenum, ruthenium, manganese and rhodium.

7. A process as claimed in claim 1 wherein said transition metal insaid cataylst is palladium, platinum or nickel.

8. A process as claimed in claim 1 wherein said catalyst is tetrakis(triphenylphosphine) palladium.

* * * * *